United States Patent [19]
Rosen et al.

[11] Patent Number: 5,922,572
[45] Date of Patent: Jul. 13, 1999

[54] POLYNUCLEOTIDES ENCODING HAEMOPOIETIC MATURATION FACTOR

[75] Inventors: Craig A. Rosen, Laytonsville; Henrik Olsen, Gaithersburg; Mark D. Adams, North Potomac, all of Md.; Ewen Kirkness, Washington, D.C.

[73] Assignee: Human Genome Sciences, Inc., Rockville, Md.

[21] Appl. No.: 08/187,186

[22] Filed: Jan. 25, 1994

[51] Int. Cl.$^6$ .......................... C07K 14/475; C12N 1/21; C12N 5/10; C12N 15/12
[52] U.S. Cl. .................... 435/69.5; 435/69.1; 435/320.1; 435/252.3; 435/325; 536/23.1; 536/23.5
[58] Field of Search .................................. 536/23.1, 23.5; 435/320.1, 69.1, 252.3, 240.1, 69.5, 325

[56] References Cited

U.S. PATENT DOCUMENTS 5,270,452 12/1993 Ramon et al. .......................... 530/399

FOREIGN PATENT DOCUMENTS 0503297 9/1992 European Pat. Off. .

OTHER PUBLICATIONS

Ngo et al. The Protein Folding Problem and Tertiary Structure Prediction. Birkhauser, Boston. pp. 491–495, 1994.
Nietro–Sampedro, M. et al., Early Release of Glia Maturation Factor and acidic Fibroblast growth Factor After Rat Brain Injury, Neuroscience Letters, 86:361–365 (1988).
Lim, R. and Zaheer, A., Structure and Function of Glia Maturation Factor Beta, Plasticity and Regeneration of the Nervous System, pp. 161–164 (1991).
Keles, G.E. et al., Expression of Glia Fibrillary Acidic Protein in Human Medulloblastoma Cells Treated with Recombinant.
Glia Maturation Factor Beta, Oncology Research, 4(10):431–437 (1992).
Zaheer, A. et al., Expression of Glia Maturation Factor Beta mRNA and Protein in Rat Organs and Cells, J. of Neurochem., 60(3):914–920 (1993).
Lim, R., et al., Cell–Surface Expression of Glia Maturation Factor Beta in Astrocytes, FASEB J., 4:3360–3363 (1990).
Lim, R. et al., Purification and Characterization of Glia Maturation Factor Beta: A Growth Regulator for Neurons and Glia Proc. Natl. Acad. Sci. USA, 86:3901–3905 (1989).
Kaplan, R. et al., Molecular Cloning and Expression of Biologically Active Human Glia Maturation Factor–Beta, J. Neurochem, 57(2):483–90 (1991).
Bosch, E.P., et al., Axonal Signals Regulate Expression of Glia Maturation Factor Beta in Schwann Cells; An immunohistochemical Study of Injured Sciatic Nerves and Cultureed Schwann Cells, J. Neurosci., 9(10): 3690–98 (1989).
Lim, R. and Miller, J.F., Sequential Interaction of Glia Maturation Factor with Insulin, Science, 22:1419–1420 (1983).
Lim, R. et al., Glia Maturation Factor Beta Regulates the Growth of N18 Neuroblastoma Cells, Dev. Biol., 137:444–450 (1990).
Lim, R. et al., Antiproliferative Function of Glia Maturation Factor Beta, Cell Regulation 1:741–6 (1990).
Bowie et al. 1990. Science 247:1306–1310.

*Primary Examiner*—John Ulm
*Assistant Examiner*—Elizabeth C. Kemmerer
*Attorney, Agent, or Firm*—Elliot M. Olstein; J. G. Mullins

[57] ABSTRACT

Disclosed is a human maturation factor polypeptide and DNA(RNA) encoding such haemopoietic maturation factor polypeptides. Also provided is a procedure for producing such polypeptide by recombinant techniques and antibodies against such polypeptide. Such polypeptides may be combined with a suitable pharmaceutical carrier or diluent to provide diagnostic, therapeutic and/or prophylactic effects against various diseases related to the underexpression of such human haemopoietic maturation factor polypeptide.

20 Claims, 6 Drawing Sheets

Purification of Haemopoietic
Maturation Factor Protein 1. 10 λ Pure Protein    4. 10 λ Pure Protein (Dif.Prep.)
2. 5 λ Pure Protein    5. Crude Protein
3. 2 λ Pure Protein

FIG. 1A

```
     AGACAGCGGAACTAAGAAAAAGAGAGGCCTGTGGACAGAACAATCATGTCTGACTCCCTG
  1  ------+---------+---------+---------+---------+---------+   60
                                                    MetSerAspSerLeu

GTGGTGTGCGAGGTAGACCCAGAGCTAACAGAAAAGCTGAGGAAATTCCGCTTCCGAAAA
 61  ------+---------+---------+---------+---------+---------+  120
     ValValCysGluValAspProGluLeuThrGluLysLeuArgLysPheArgLys

GAGACAGACAATGCAGCCATCATAATGAAGGTGGACAAAGACCGGCAGATGGTGGTGCTG
121  ------+---------+---------+---------+---------+---------+  180
     GluThrAspAsnAlaAlaIleIleMetLysValAspLysAspArgGlnMetValValLeu

GAGGAAGAATTTCAGAACATTCCCCAGAGGAGCTCAAAAATGGAGTTGCCGGAGAGACAG
181  ------+---------+---------+---------+---------+---------+  240
     GluGluGluPheGlnAsnIleSerProGluLeuLeuLysMetGluLeuProGluArgGln

CCCAGGTTCGTGGTTTACAGCTACAAGTACGTGCATGACGATGGCCGAGTGTCCTACCCT
241  ------+---------+---------+---------+---------+---------+  300
     ProArgPheValValTyrSerTyrLysTyrValHisAspAspGlyArgValSerTyrPro
```

FIG. 1B

```
301  TTGTGTTTCATCTTCTCCCAGCCCTGTGGGCTGCAAGCCCGGAACAACAGATGATGTATGCA  360
     ----+----+----+----+----+----+----+----+----+----+----+----+
     LeuCysPheIlePheSerSerProValGlyCysLysProGluGlnMetMetTyrAla

361  GGGAGTAAAAACAGGCTGGTGCAGACAGCAGAGCTCACAAAGGTGTTCGAAATCCGCACC  420
     ----+----+----+----+----+----+----+----+----+----+----+----+
     GlySerLysAsnArgLeuValGlnThrAlaGluLeuThrLysValPheGluIleArgThr

421  ACTGATGACCTCACTGAGGCCTGGCTCCAAGAAAAGTTGTCTTTCTTTCGTTGATCTCTG  480
     ----+----+----+----+----+----+----+----+----+----+----+----+
     ThrAspAspLeuThrGluAlaTrpLeuGlnGluLysLeuSerPhePheArg

481  GGCTGGGGACTGAATTCCCTGATGTCTGAGTCCTCAAGGTGACTGGGGACTTGGAACCCCT  540
     ----+----+----+----+----+----+----+----+----+----+----+----+

541  AGGACCTGAACAACCAAGACTTTAAATAAATTTTTAAATGCAAAAAAAAAAAAAAAAAAA  600
     ----+----+----+----+----+----+----+----+----+----+----+----+
```

FIG. 2

```
Query:   46 MSDSLVVCEVDPELTEKLRKFRFRKETDNAAIIMKVDKDRQMVVLEEEFQNISPEELKME 225
             MS+SLVVC+V   +L EKLRKFRFRKET+NAAIIMK+DKD+++VVL+EE + ISP+ELK E
Sbjct:    1 MSESLVVCDVAEDLVEKLRKFRFRKETNNAAIIMKIDKDKRLVVLDEELEGISPDELKDE 60

Query:  226 LPERQPRFVVYSYKYVHDDGRVSYPLCFIFSSPVGCKPEQQMMYAGSKNRLVQTAELTKV 405
            LPERQPRF+VYSYKY HDDGRVSYPLCFIFSSPVGCKPEQQMMYAGSKN+LVQTAELTKV
Sbjct:   61 LPERQPRFIVYSYKYQHDDGRVSYPLCFIFSSPVGCKPEQQMMYAGSKNKLVQTAELTKV 120

Query:  406 FEIRTTDDLTEAWLQEKLSFF 468
            FEIR T+DLTE WL+EKL FF
Sbjct:  121 FEIRNTEDLTEEWLREKLGFF 141
```

FIG. 3

Purification of Haemopoietic Maturation Factor Protein 1. 10 λ Pure Protein
2. 5 λ Pure Protein
3. 2 λ Pure Protein
4. 10 λ Pure Protein (Dif.Prep.)
5. Crude Protein

FIG. 4

Northern Blot
Haemopoietic Maturation Factor

M 1 2 3 4 5 6 7 8

2.4 kb —

0.9 kb —

1. Spleen     4. Testes     7. Colon
2. Thymus     5. Ovary     8. Leukocytes
3. Prostate     6. Small Intestine

FIG. 5

Haemopoietic growth factor and HeLa cell growth

| Experiment # | Exp.1 | Exp.2 | Exp.3 |
|---|---|---|---|
| Cell Number | (x10$^5$; SD) [% cntl] | (x10$^4$; SD) [% cntl] | (x10$^4$; SD) [% cntl] |

Haemopoietic growth factor (μg/ml).

| | | | |
|---|---|---|---|
| 0 | 3.2; 0.2 | 6.0; 0.3 [100] | 5.1; 0.3 [90] |
| 0.1 | 2.9; 0.3 [91] | 6.0; 0.3 [100] | 4.6; 0.3 [86] |
| 1.0 | 2.9; 0.3 [91] | 4.2; 0.3 [70] | 4.4; 0.5 [45] |
| 10.0 | 1.5; 0.2 [47] | 3.7; 0.6 [62] | 2.3; 0.2 [45] |

SD; standard deviation
[% cntl]; percent cells compared to untreated (oμg/ml haemopoietic growth factor).

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:

(A) LENGTH: 600 BASE PAIRS
        (B) TYPE: NUCLEIC ACID
        (C) STRANDEDNESS: SINGLE
        (D) TOPOLOGY: LINEAR (ii) MOLECULE TYPE: cDNA (xi) SEQUENCE DESCRIPTION: SEQ ID NO:1:

```
AGACAGCGGA ACTAAGAAAA GAAGAGGCCT GTGGACAGAA CAATCATGTC TGACTCCCTT     60

GTGGTGTGCG AGGTAGACCC AGAGCTAACA GAAAAGCTGA GGAAATTCCG CTTCCGAAAA    120

GAGACAGACA ATGCAGCCAT CATAATGAAG GTGGACAAAG ACCGGCAGAT GGTGGTGCTG    180

GAGGAAGAAT TCAGAACAT TTCCCCAGAG GAGCTCAAAA TGGAGTTGCC GGAGAGACAG     240

CCCAGGTTCG TGGTTTACAG CTACAAGTAC GTGCATGACG ATGGCCGAGT GTCCTACCCT    300

TTGTGTTTCA TCTTCTCCAG CCCTGTGGGC TGCAAGCCGG AACAACAGAT GATGTATGCA    360

GGGAGTAAAA ACAGGCTGGT GCAGACAGCA GAGCTCACAA AGGTGTTCGA AATCCGCACC    420

ACTGATGACC TCACTGAGGC CTGGCTCCAA GAAAAGTTGT CTTTCTTTCG TTGATCTCTG    480

GGCTGGGGAC TGAATTCCTG ATGTCTGAGT CCTCAAGGTG ACTGGGGACT GGAACCCCT    540

AGGACCTGAA CAACCAAGAC TTTAAATAAA TTTTTAAATG CAAAAAAAAA AAAAAAAAA    600
```

(2) INFORMATION FOR SEQ ID NO:2:

(i) SEQUENCE CHARACTERISTICS:
        (A) LENGTH: 142 AMINO ACIDS
        (B) TYPE: AMINO ACID
        (C) STRANDEDNESS:
        (D) TOPOLOGY: LINEAR (ii) MOLECULE TYPE: PROTEIN (xi) SEQUENCE DESCRIPTION: SEQ ID NO:2:

```
Met Ser Asp Ser Leu Val Val Cys Glu Val Asp Pro Glu Leu Thr
              5                  10                  15

Glu Lys Leu Arg Lys Phe Arg Phe Arg Lys Glu Thr Asp Asn Ala
             20                  25                  30

Ala Ile Ile Met Lys Val Asp Lys Asp Arg Gln Met Val Val Leu
             35                  40                  45

Glu Glu Glu Phe Gln Asn Ile Ser Pro Glu Glu Leu Lys Met Glu
             50                  55                  60

Leu Pro Glu Arg Gln Pro Arg Phe Val Val Tyr Ser Tyr Lys Tyr
             65                  70                  75

Val His Asp Asp Gly Arg Val Ser Tyr Pro Leu Cys Phe Ile Phe
             80                  85                  90

Ser Ser Pro Val Gly Cys Lys Pro Glu Gln Gln Met Met Tyr Ala
             95                 100                 105

Gly Ser Lys Asn Arg Leu Val Gln Thr Ala Glu Leu Thr Lys Val
            110                 115                 120

Phe Glu Ile Arg Thr Thr Asp Asp Leu Thr Glu Ala Trp Leu Gln
            125                 130                 135

Glu Lys Leu Ser Phe Phe Arg
            140
```

(2) INFORMATION FOR SEQ ID NO:3:

(i) SEQUENCE CHARACTERISTICS:
        (A) LENGTH: 93 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:3:

GACTTCATGA AAAAGACAGA TATCGCAATT GCAGTGGCAC TGGCTGGTTT CGCTACCGTT      60

GCGCAAGCTG CTTCTGACTC CCTGGTGGTG TGC      93

(2) INFORMATION FOR SEQ ID NO:4:

(i) SEQUENCE CHARACTERISTICS:
        (A) LENGTH: 31 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:4:

GACTAGATCT ACGAAAGAAA GACAACTTTT C      31

(2) INFORMATION FOR SEQ ID NO:5:

(i) SEQUENCE CHARACTERISTICS:
        (A) LENGTH: 141 AMINO ACIDS
        (B) TYPE: AMINO ACID
        (C) STRANDEDNESS:
        (D) TOPOLOGY: LINEAR (ii) MOLECULE TYPE: PROTEIN (xi) SEQUENCE DESCRIPTION: SEQ ID NO:5:

Met Ser Glu Ser Leu Val Val Cys Asp Val Ala Glu Asp Leu Val
                 5                  10                  15

Glu Lys Leu Arg Lys Phe Arg Phe Arg Lys Glu Thr Asn Asn Ala
                20                  25                  30

Ala Ile Ile Met Lys Ile Asp Lys Asp Lys Arg Leu Val Val Leu
                35                  40                  45

Asp Glu Glu Lys Glu Gly Ile Ser Pro Asp Glu Leu Lys Asp Glu
                50                  55                  60

Leu Pro Glu Arg Gln Pro Arg Phe Ile Val Tyr Ser Tyr Lys Tyr
                65                  70                  75

Asn His Asp Asp Gly Arg Val Ser Tyr Pro Leu Cys Phe Ile Phe
                80                  85                  90

Ser Ser Pro Val Gly Cys Lys Pro Glu Gln Gln Met met Tyr Ala
                95                 100                 105

Gly Ser Lys Asn Lys Leu Val Gln Thr Ala Glu Leu Thr Lys Val
               110                 115                 120

Phe Glu Ile Arg Asn Thr Glu Asp Leu Thr Glu Glu Trp Leu Arg
               125                 130                 135

Glu Lys Leu Gly Phe Phe
               140

POLYNUCLEOTIDES ENCODING HAEMOPOIETIC MATURATION FACTOR

This invention relates to newly identified polynucleotide sequences, polypeptides encoded by such sequences, the use of such polynucleotides and polypeptides, as well as the production of such polynucleotides and polypeptides. More particularly, the polypeptide of the present invention is a haemopoietic factor. Various growth factors have been discovered, studied and utilized (cellular and molecular biology, edited by the Japanese Tissue Culture Association, Asakura Shoten (1987). Such cell growth factors include epidermal growth factor, platelet derived growth factor, acidic fibroblast growth factor and basic fibroblast growth factor. All these factors have been isolated based upon growth promotion of fibroblast cells. However, these factors have also been found to display widely ranging activity and poor specificity.

Accordingly, recent attempts have been made to search for growth factors specifically acting on functionally differentiated cells. As a result, growth factors such as keratinocyte growth factor and hepatocyte growth factor have been isolated, thus creating the possibility that these factors could be used to treat diseases vulnerable to their specific action spectra. Another growth factor which has been isolated is disclosed in European Patent Application No. 92102385.9 applied for by Takeda Chemical Industries, Ltd. disclosing a glia activating factor which has glial cell growth promoting activity, and the DNA encoding for that polypeptide.

Haematopoiesis is the production of blood cells. The major haematopoietic tissues are bone marrow, spleen, lymph nodes and thymus. Haematopoiesis in the human embryo begins in the second week of life. Bone marrow appears in the embryo in the second month, and it becomes the dominant haematopoietic organ in the latter half of gestation and throughout postnatal life. The bone marrow contains stem cells that give rise to all cells of the haemopoietic series. All of the blood cells except T-lymphocytes are produced in the marrow. Haematopoietic stems cells differentiate into the mature blood cells in response to the action of haemopoietic maturation factor. Accordingly, a haematopoietic growth factor which could be purified and isolated, would have extensive therapeutic value in the treatment and diagnosis of blood cell and other diseases.

In accordance with one aspect of the present invention, there is provided a novel polypeptide which is a haemopoietic maturation factor, as well as analogs and derivatives thereof. The haemopoietic maturation factor of the present invention is of human origin.

In accordance with another aspect of the present invention, there is provided a polynucleotide (DNA or RNA) which encodes such polypeptide.

In accordance with still another aspect of the present invention, there is provided a procedure for producing such polypeptide by recombinant techniques.

In accordance with yet a further aspect of the present invention, there is provided a process for utilizing such polypeptide, or DNA sequence encoding such polypeptide for therapeutic purposes, for example stimulating differentiation and proliferation of cells of haemopoietic or neural origin.

In accordance with yet another aspect of the present invention, there is provided an antibody against the haemopoietic maturation factor.

In accordance with yet another aspect of the present invention, there is provided a composition which is employed as an antagonist to haemopoietic maturation factor, e.g., an antibody against such polypeptide which may be used to inhibit the action of such polypeptide, for example, in the treatment of T-cell deficient related disorders.

These and other aspects of the present invention should be apparent to those skilled in the art from the teachings herein.

BRIEF DESCRIPTION OF THE DRAWINGS

The following drawings are meant only as illustrations of specific embodiments of the present invention and are not meant as limitations in any manner.

BRIEF DESCRIPTION OF THE INVENTION

Figure 1A:
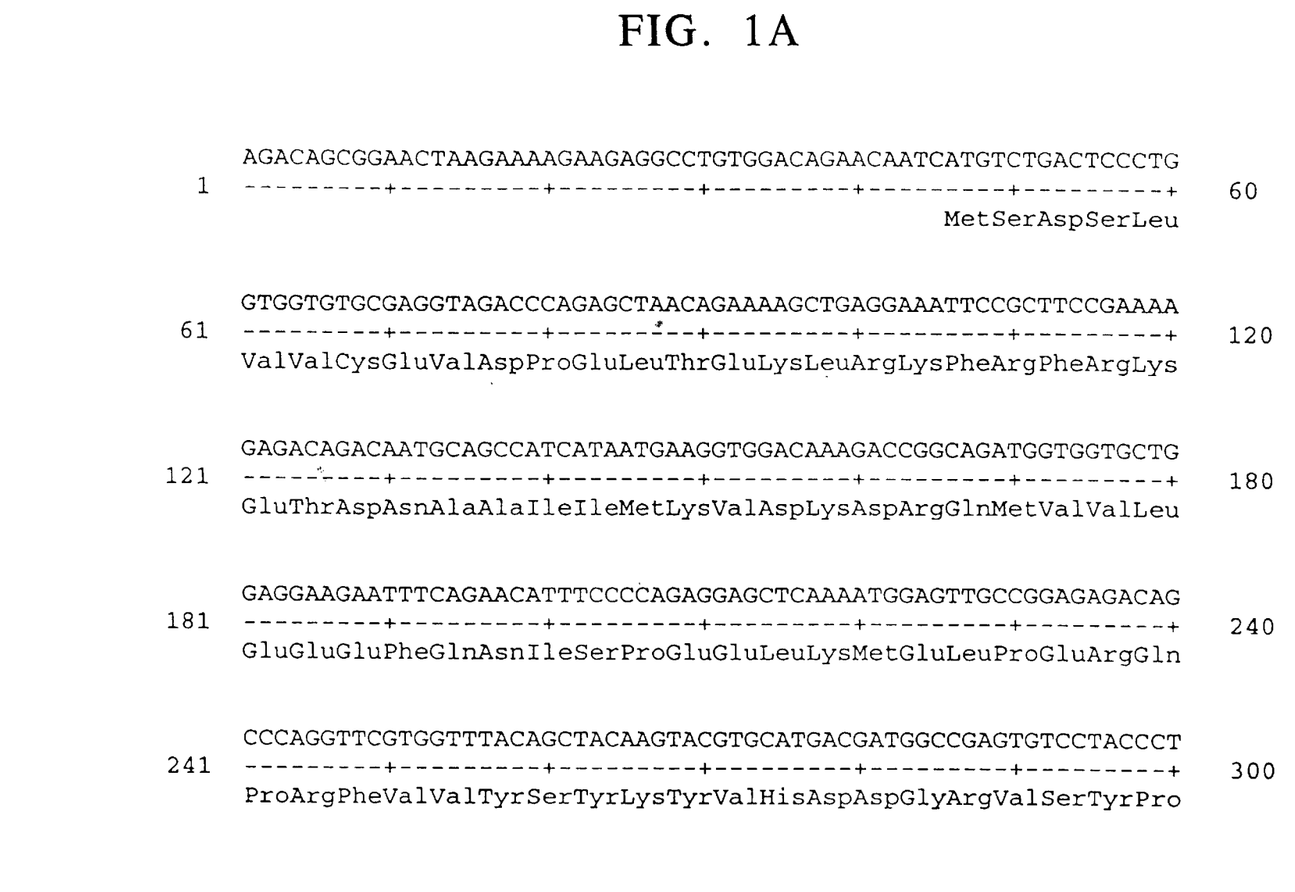
FIG. 1 shows the polynucleotide sequence (SEQ ID NO:1) which encodes for the haemopoietic maturation factor polypeptide (SEQ ID NO:2). It also shows the amino acid sequence of the haemopoietic maturation factor polypeptide. The standard three letter abbreviation has been used to depict the amino acid sequence.
Figure 1B:
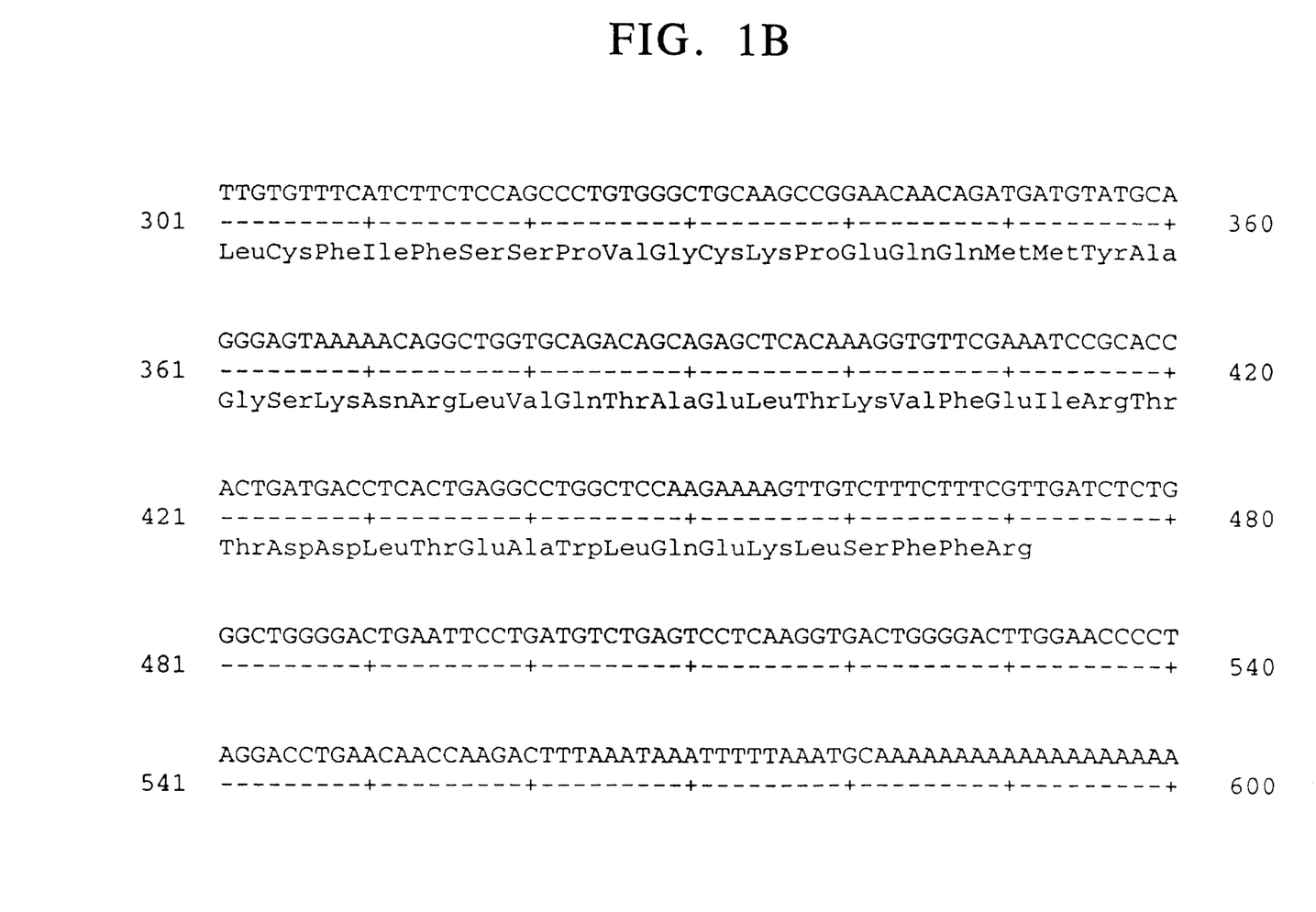
Figure 2:
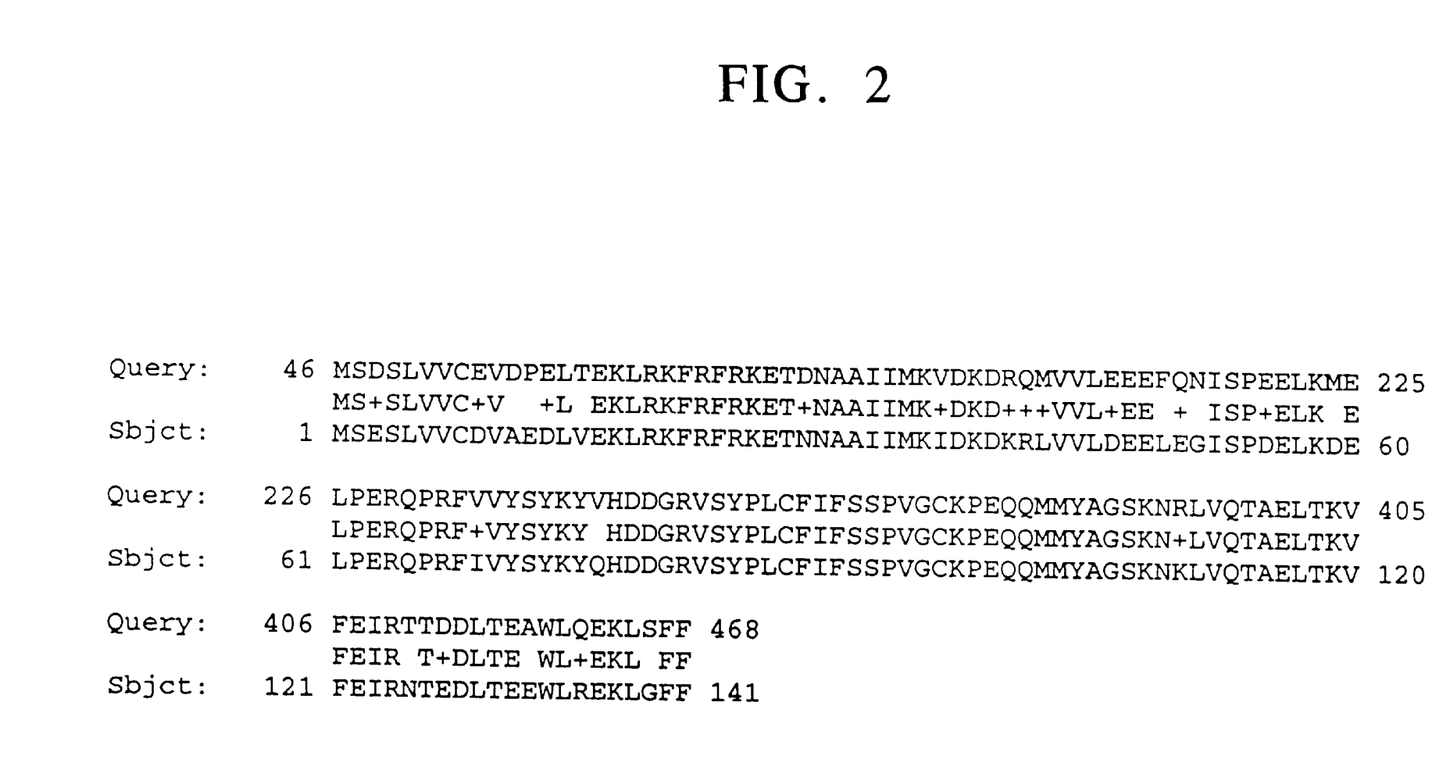
FIG. 2 shows the homology of the haemopoietic maturation factor (SEQ ID NO:2) to glia maturation factor β SEQ ID NO:3.
Figure 3:
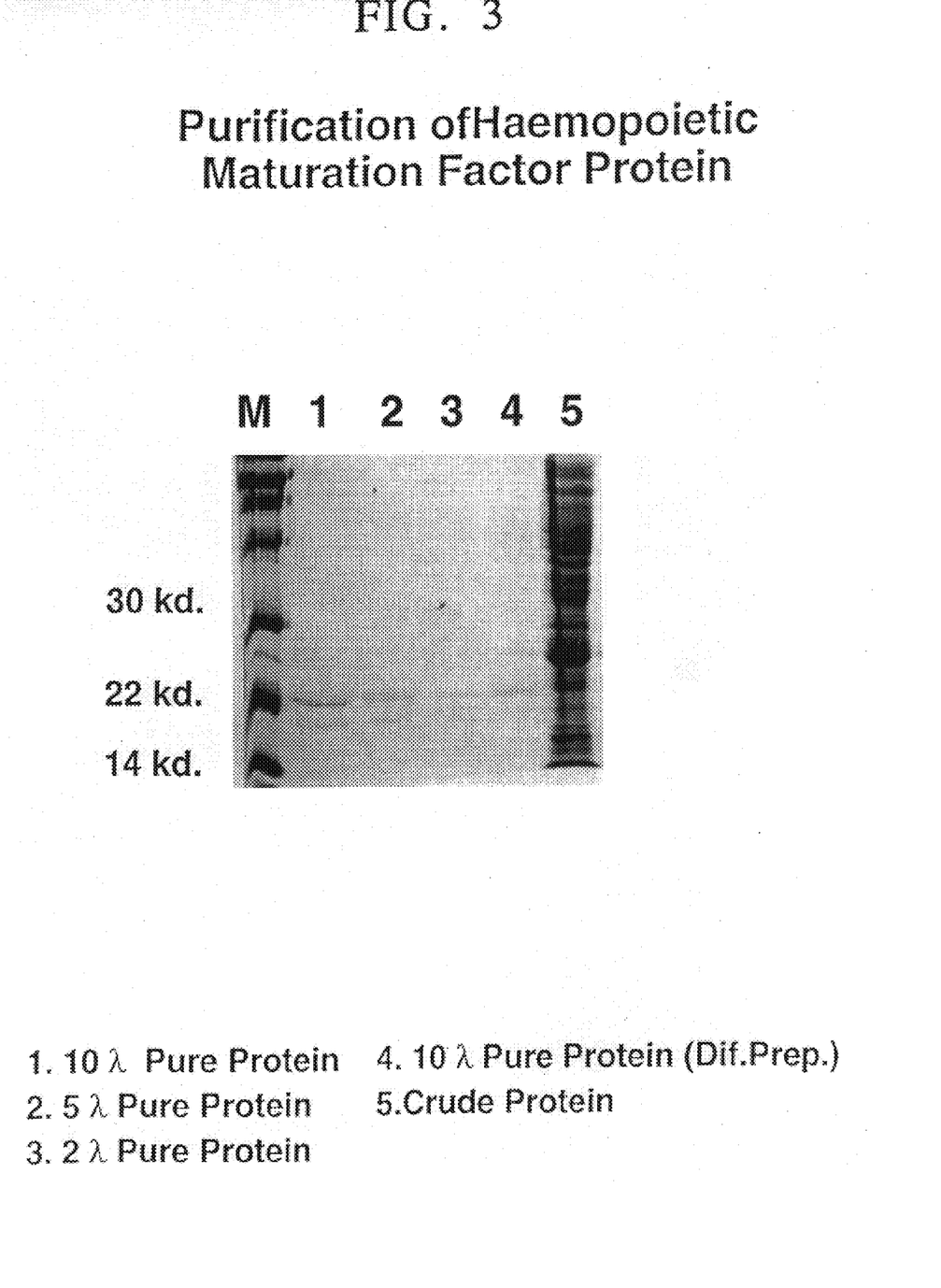
FIG. 3 illustrates the banding characteristics of the purified haemopoietic maturation factor protein after bacterial expression, and purification.

In accordance with one aspect of the present invention, there is provided a DNA sequence (and corresponding RNA sequence) as set forth in FIG. 1 of the drawings and/or DNA (RNA) sequences encoding the same polypeptide as the sequence of FIG. 2 of the drawings, as well as fragment portions, derivatives, analogs and all allelic variants of such sequences.

In accordance with another aspect of the present invention, there is provided a polynucleotide which encodes the same polypeptide as the polynucleotide of the cDNA clone deposited as ATCC deposit number 75514, deposited on Aug. 4, 1993, and/or fragments, analogs, derivatives or allelic variants of such polynucleotide.

In the case of DNA, DNA may be single stranded or double stranded, and if single stranded the DNA sequence may be the "sense" strand shown in FIG. 1 or the one complementary thereto.

The polynucleotide (DNA or RNA, preferably DNA) includes at least the portion coding for the polypeptide, which coding portion may be the same as that in the deposited clone or may be different than that in the deposited clone provided that it encodes for the same polypeptide or an allelic variant thereof. The coding portion preferably encodes at least the mature form of the protein of the present invention.

The present invention further relates to polynucleotide sequences which hybridize to the hereinabove-described polynucleotide sequences if there is at least 50% and preferably at least 70% identity between the sequences. In another preferred embodiment, the present invention relates to polynucleotide sequences which hybridize under stringent conditions to the hereinabove-described polynucleotide sequences. As herein used, the term "stringent conditions"

means hybridization will occur if there is at least 95% and preferably at least 97% identity between the segments. Thus, the present invention includes DNA (RNA) sequences encoding allelic variant forms of the peptide encoded by the DNA of FIG. 1. Thus, the present invention provides isolated DNA (RNA) encoding for a naturally occurring human polypeptide which is a haemopoietic maturation factor, as well as allelic variants thereof.

The present invention further relates to a polypeptide which is a haemopoietic maturation factor, and which has the structure shown in FIG. 2, as well as allelic variants thereof, and analogs, fragments and derivatives thereof which have the same function as the naturally occurring polypeptide.

The polypeptide of the present invention is mainly expressed in haemopoietic tissues and, as such, represents an haemopoietic maturation factor for controlling cells of haemopoietic origin and cells with which they interact.

The present invention further relates to a polypeptide encoded by the DNA contained in the clone deposited as ATCC number 75514 on Aug. 4, 1993 as well as analogs, fragments, derivatives and allelic variants thereof. These deposits will be maintained under the Budapest Treaty on the International Recognition of the Deposit of Microorganisms for the purposes of Patent Procedure. These deposits are provided merely as a convenience and are not an admission that a deposit is required under 35 U.S.C. § 112. The sequence of the polynucleotides contained in the deposited materials, as well as the amino acid sequence of the polypeptides encoded thereby, are incorporated herein by reference and are controlling in the event of any conflict with the description of sequences herein. A license may be required to make, use or sell the deposited materials, and no such license is hereby granted.

The ATCC number referred to above is directed to a biological deposit with the ATCC, 12301 Parklawn Drive, Rockville, Md. 20852. The strain referred to is being maintained under the terms of the Budapest Treaty and will be made available to a patent office signatory to the Budapest Treaty.

The polypeptide of the present invention is preferably provided in an isolated form, and preferably is purified.

The term "isolated" means that the material is removed from its original environment (e.g., the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that such vector or composition is not part of its natural environment.

In a preferred embodiment, the haemopoietic maturation factor is a full length mature human haemopoietic maturation factor or an allelic or glycosylated variant thereof. The polynucleotide may also encode a preprotein which is processed and secreted from mammalian cells as the mature protein.

The polynucleotide sequence of the present invention may encode for a mature form of the polypeptide or it may also encode for a leader sequence which facilitates secretion of the polypeptide. For example, the desired DNA sequence may be fused in the same reading frame to a DNA sequence which aids in secretion of the polypeptide, for example a leader sequence which functions as a secretory sequence for controlling transport of the polypeptide from the cell of the host. The protein having a leader sequence is a preprotein and may have the leader sequence cleaved by the host cell to form the mature form of the protein. The polynucleotide of the present invention may also be fused in frame to a marker sequence, for example, a histidine tag, which allows for purification of the polypeptide.

Thus, the polypeptide(s) of the present invention may be the mature form of the haemopoietic maturation factor of the present invention; or may be in the form of a preprotein or prepolypeptide wherein the mature polypeptide includes a leader or secretory sequence; or may be in the form of a fusion protein wherein additional amino acids which aid in, for example, purification of the polypeptide are fused to the mature or preprotein at either the 3' or 5' end thereof.

In a preferred embodiment of the present invention, the marker sequence is a hexa-histidine tag added to the coding frame by a bacterial expression vector.

The polypeptide of the present invention is found predominantly in the spleen and thymus and is most concentrated in the leukocytes.

As hereinabove indicated, the present invention also includes variants of the polypeptide which is encoded by the DNA of FIG. 1 and/or variants of the DNA contained in the deposited clone, which retains the qualitative activity of such a polypeptide which is a haemopoietic maturation factor. The variant may be a substitutional variant, or an insertion variant or a deletional variant. Such variants can be naturally occurring allelic variants such as for example, those with different glycosylation patterns or substitution at the amino acid level or deletion at the amino acid level.

Such variants may also be produced by site specific mutagenesis. The substitutional variant may be a substituted conserved amino acid or a substituted non-conserved amino acid, and preferably a conserved amino acid.

A polynucleotide encoding a polypeptide of the present invention may be obtained from a cDNA library derived from human early stage kidney tissue, spleen, thymus, or from leukocytes. It contains an open reading frame encoding a mature protein of 142 amino acids in length. The amino acid of the haemopoietic maturation factor has sequence homology to a known growth factor isolated from neural cells. The polypeptide encoded by the polynucleotide is structurally related to human glia maturation factor with 82% identical amino acids and 92% similarity over the entire region. It is also structurally related to bovine glia maturation factor with 82% identical amino acids and 92% similarity over the entire coding region. The polypeptide may be found on the surface of T-cells.

Glia maturation factor is a 17 kd protein found in the brain of mammals with no apparent sequence homology to other known proteins. It is most abundant in the embryo but is also found in later stages of development. The human glial maturation factor controls the differentiation and proliferation of certain cells of neural origin.

Host cells are transformed with the expression vectors of this invention and cultured in conventional nutrient media modified as appropriate for inducing promoters, selecting transformants or amplifying the haemopoietic maturation factor gene. The culture conditions, such as temperature, pH and the like, are those previously used with the host cell selected for expression, and will be apparent to the ordinarily skilled artisan.

"Transformation" means introducing DNA into an organism so that the DNA is replicable, either as an extrachromosomal element or by chromosomal integration. Unless indicated otherwise, the method used herein for transformation of the host cells is the method of Graham, F. and van der Eb, A., *Virology* 52:456–457 (1973). However, other methods for introducing DNA into cells such as by nuclear injection or by protoplast fusion may also be used. If prokaryotic cells or cells which contain substantial cell wall constructions are used, the preferred method of transfections is calcium treatment using calcium chloride as described by Cohen, F. N. et al., *Proc. Natl. Acad. Sci.* (USA), 69:2110 (1972).

"Transfection" refers to the introduction of DNA into a host cell whether or not any coding sequences are ultimately expressed. Cells do not naturally take up DNA. Thus, a variety of technical "tricks" are utilized to bypass natural barriers to gene transfer. Numerous methods of transfection are known to the ordinarily skilled artisan, for example, $CaPO_4$ and electroporation. Transformation of the host cell is the indicia of successful transfection.

The polynucleotide of the present invention may be employed for producing a polypeptide by recombinant techniques. Thus, for example, the polynucleotide sequence may be included in any one of a variety of vectors or plasmids for expressing a polypeptide. Such vectors include chromosomal, nonchromosomal and synthetic DNA sequences, e.g., derivatives of SV40; bacterial plasmids; phage DNA's; yeast plasmids; vectors derived from combinations of plasmids and phage DNAs, viral DNA such as vaccinia, adenovirus, fowl pox virus, and pseudorabies. However, any other plasmid or vector may be used as long as it is replicable and viable in the host.

As hereinabove described, the appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli*. lac or trp, the phage lambda PL promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain a gene to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli, Salmonella typhimurium*; fungal cells, such as yeast; animal cells such as CHO or Bowes melanoma; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter and an enhancer, operably linked to the sequence. Large numbers of suitable vectors and promoters are known to those of skill in the art, and are commercially available. The following vectors are provided by way of example. Bacterial: pQE-9 (Qiagen), pBs, phagescript, PsiX174, pBluescript SK, pBsKS, pNH8a, pNH16a, pNH18a, pNH46a (Stratagene); pTrc99A, pKK223-3, pKK233-3, pDR540, pRIT5 (Pharmacia). Eukaryotic: pWLneo, pSV2cat, pOG44, pXT1, pSG (Stratagene) pSVK3, pBPV, pMSG, pSVL (Pharmacia). However, any other plasmid or vector may be used as long as it is replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, and trc. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described construct. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE, dextran mediated transfection, or electroporation (Davis, L., Dibner, M., Battey, I., *Basic Methods in Molecular Biology*, 1986).

The constructs in host cells can be used in a conventional manner to produce the gene product coded by the recombinant sequence. Alternatively, the encoded polypeptide can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., *Molecular Cloning: A Laboratory Manual*, Second Edition, (Cold Spring Harbor, N.Y., 1989), the disclosure of which is hereby incorporated by reference.

Transcription of a DNA encoding the polypeptides of the present invention by higher eukaryotes is increased by inserting an enhancer sequence into the vector. Enhancers are cis-acting elements of DNA, usually about from 10 to 300 bp, that act on a promoter to increase its transcription. Examples include the SV40 enhancer on the late side of the replication origin (bp 100 to 270), a cytomegalovirus early promoter enhancer, a polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These PBR322 "backbone" sections are combined with an appropriate promoter and the structural sequence to be expressed.

Following transformation of a suitable host strain and growth of the host strain to an appropriate cell density, the selected promoter is derepressed by appropriate means (e.g., temperature shift or chemical induction) and cells are cultured for an additional period. Cells are typically harvested by centrifugation, disrupted by physical or chemical means, and the resulting crude extract retained for further purification.

Haemopoietic maturation factor is recovered and purified from recombinant cell cultures by methods used heretofore, including ammonium sulfate or ethanol precipitation, acid extraction, anion or cation exchange chromatography, phosphocellulose chromatography, hydrophobic interaction chromatography, affinity chromatography (e.g., using DNA or nucleotides on a solid support), hydroxyapatite chromatography and lectin chromatography. It is preferred to have low concentrations (approximately 0.1–5 mM) of calcium ion present during purification (Price, et al., *J. Biol. Chem.*, 244:917 (1969)).

Various mammalian cell culture systems can also be employed to express recombinant protein. Examples of mammalian expression systems include the COS-7 lines of monkey kidney fibroblasts, described by Gluzman, *Cell*, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements.

Recombinant protein produced in bacterial culture is usually isolated by initial extraction from cell pellets, followed by one or more salting-out, aqueous ion exchange or size exclusion chromatography steps. Protein refolding steps can be used, as necessary, in completing configuration of the mature protein. Finally, high performance liquid chromatography (HPLC) can be employed for final purification steps. Microbial cells employed in expression of proteins can be disrupted by any convenient method, including freeze-thaw cycling, sonication, mechanical disruption, or use of cell lysing agents.

The polypeptide of the present invention may be a naturally purified product, or a product of chemical synthetic procedures, or produced by recombinant techniques from a prokaryotic or eukaryotic host (for example, by bacterial, yeast, higher plant, insect and mammalian cells in culture) of a polynucleotide sequence of the present invention. Depending upon the host employed in a recombinant production procedure, the polypeptides of the present invention may be glycosylated with mammalian or other eukaryotic carbohydrates or may be non-glycosylated. Polypeptides of the invention may also include an initial methionine amino acid residue (at position minus 1).

In addition to naturally occurring allelic forms of the polypeptide, the present invention also embraces analogs and fragments thereof, which also function as a haemopoietic maturation factor. Thus, for example, one or more of the amino acid residues of the polypeptide may be replaced by conserved amino acid residues.

The haemopoietic maturation factor may be used in the treatment of abnormalities of neural or haemopoietic origin, for example cancer, since the haemopoietic maturation factor may block or retard the growth of cancerous cells.

The polypeptide of the present invention may also be used for treating leukemia. Leukemia is clinically featured by suppression of normal blood cell formation resulting from suppression of normal haemopoiesis by factors produced by leukemic cells. This results in anemia, thrombocytopenia and granulocytopenia. Accordingly, administration of a therapeutically effective amount of haemopoietic maturation factor may be used to overcome the suppression of haemopoiesis by leukemic cells. Haemopoietic maturation factor may also be used for treating other blood related disorders, e.g., hemolysis, polycythemia vera, melogibrosis, hemophilia, and splenomegaly.

Haemopoietic maturation factor may be used in the stimulation of differentiation of mature blood cells in situations where a patient has undergone a bone marrow transplant due to a cancer or other situation. Haemopoietic maturation factor may also be used to stimulate bone marrow cells in vitro for research and diagnostic purposes.

The polypeptide of the present invention may also be employed in accordance with the present invention by expression of such polypeptide in vivo, which is often referred to as "gene therapy."

Thus, for example, cells such as bone marrow cells may be transduced with a polynucleotide (DNA or RNA) encoding for the polypeptide ex vivo, the transduced cells are then provided to a patient to be treated with the polypeptide. Such methods are well-known in the art. For example, cells may be transduced by procedures known in the art by use of a retroviral particle containing RNA encoding for the polypeptide of the present invention.

Similarly, transduction of cells may be accomplished in vivo for expression of the polypeptide in vivo, for example, by procedures known in the art. As known in the art, a producer cell for producing a retroviral particle containing RNA encoding the polypeptide of the present invention may be administered to a patient for transduction in vivo and expression of the polypeptide in vivo.

These and other methods for administering a polypeptide of the present invention by such methods should be apparent to those skilled in the art from the teachings of the present invention. For example, the expression vehicle for transducing cells may be other than a retroviral particle, for example, an adenovirus, which may be used to transduce cells in vivo after combination with a suitable delivery vehicle.

The polypeptide of the present invention may be employed in combination with a suitable pharmaceutical carrier. Such compositions comprise a therapeutically effective amount of the protein, and a pharmaceutically acceptable carrier or excipient. Such a carrier includes but is not limited to saline, buffered saline, dextrose, water, glycerol, ethanol, and combinations thereof. The formulation should suit the mode of administration.

An injection of a composition containing the haemopoietic maturation factor may be prepared by conventional methods using, for example, physiological saline or aqueous solutions containing glucose or other auxiliary agents. The pharmaceutical compositions such as tablets and capsules can also be prepared in accordance with conventional methods. The injections, solutions, tablets and capsules as the pharmaceutical compositions are prepared under aseptic conditions.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptide of the present invention may be employed in conjunction with other therapeutic compounds.

When the haemopoietic maturation factor of the present invention is used as a pharmaceutical, it can be given to mammals (such as humans, mice, rats, hamster, dogs, rabbits and cats), in a suitable vehicle.

When the polypeptide of the present invention is used as a pharmaceutical as described above, it is given, for example, to the above-mentioned subjects in therapeutically effective doses of at least about 10 µg/kg body weight and in most cases it would be administered in an amount not in excess of about 8 mg/kg body weight per day and preferably the dosage is from about 10 µg/kg body weight to about 1 mg/kg body weight daily, taking into account the routes of administration, symptoms, etc.

Each of the cDNA sequences identified herein or a portion thereof can be used in numerous ways as polynucleotide reagents. The sequences can be used as diagnostic probes for the presence of a specific mRNA in a particular cell type. In addition, these sequences can be used as diagnostic probes suitable for use in genetic linkage analysis (polymorphisms).

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of cDNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 500 or 600 bases; however, clones larger than 2,000 bp have a higher likelihood of binding to a unique chromosomal location with sufficient signal intensity for simple detection. FISH requires use of the clone from which the EST was derived, and the longer the better. For example, 2,000 bp is good, 4,000 is better, and more than 4,000 is probably not necessary to get good results a reasonable percentage of the time. For a review of this technique, see Verma et al., *Human Chromosomes: a Manual of Basic Techniques*, Pergamon Press, New York (1988).

Once a sequence has been mapped to a precise chromosomal location, the physical position of the sequence on the chromosome can be correlated with genetic map data. (Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Comparison of affected and unaffected individuals generally involves first looking for structural alterations in the chromosomes, such as deletions or translocations that are visible from chromosome spreads or detectable using PCR based on that cDNA sequence. Ultimately, complete sequencing of genes from several individuals is required to confirm the presence of a mutation and to distinguish mutations from polymorphisms.

The present invention is further directed to inhibiting haemopoietic maturation factor in vivo to reduce and/or eliminate its stimulatory effect by use of antisense technology. Antisense technology can be used to control gene expression through triple-helix formation or antisense DNA or RNA, both of which methods are based on binding of a polynucleotide sequence to DNA or RNA. For example, the 5' coding portion of the polynucleotide sequence, which encodes for the polypeptide of the present invention, is used to design an antisense RNA oligonucleotide of from 10 to 40 base pairs in length. A DNA oligonucleotide is designed to be complementary to a region of the gene involved in transcription (triple helix—see Lee et al, *Nucl. Acids Res.,* 6:3073 (1979); Cooney et al, *Science,* 241:456 (1988); and Dervan et al, *Science,* 251: 1360 (1991), thereby preventing transcription and the production of haemopoietic maturation factor.

The antisense RNA oligonucleotide hybridizes to the mRNA in vivo and blocks translation of an mRNA molecule into the haemopoietic maturation factor (antisense—Okano, *J. Neurochem.,* 56:560 (1991); *Oligodeoxynucleotides as Antisense Inhibitors of Gene Expression,* CRC Press, Boca Raton, Fla. (1988)).

Alternatively, the oligonucleotides described above can be delivered to cells by procedures in the art such that the anti-sense RNA or DNA may be expressed in vivo to inhibit production of haemopoietic maturation factor in the manner described above.

Antisense constructs to haemopoietic maturation factor, therefore, may stimulate cell growth which may be used for treating certain disorders, for example, AIDS, since blocking haemopoietic maturation factor may control T-cell maturation. In this way, antisense constructs may also be used to treat anemia.

The protein, its fragments or other derivatives, or analogs thereof, or cells expressing them can be used as an immunogen to produce antibodies thereto. These antibodies can be, for example, polyclonal, monoclonal, chimeric, single chain, Fab fragments, or the product of an Fab expression library. Various procedures known in the art may be used for the production of polyclonal antibodies.

Antibodies generated against the polypeptide corresponding to a sequence of the present invention can be obtained by direct injection of the polypeptide into an animal or by administering the polypeptide to an animal, preferably a nonhuman. The antibody so obtained will then bind the polypeptide itself. In this manner, even a sequence encoding only a fragment of the polypeptide can be used to generate antibodies binding the whole native polypeptide. Such antibodies can then be used to isolate the polypeptide from tissue expressing that polypeptide. Moreover, a panel of such antibodies, specific to a large number of polypeptides, can be used to identify and differentiate such tissue.

For preparation of monoclonal antibodies, any technique which provides antibodies produced by continuous cell line cultures can be used. Examples include the hybridoma technique (Kohler and Milstein, 1975, *Nature,* 256:495–497), the trioma technique, the human B-cell hybridoma technique (Kozbor et al., 1983, *Immunology Today* 4:72), and the EBV-hybridoma technique to produce human monoclonal antibodies (Cole, et al., 1985, in *Monoclonal Antibodies and Cancer Therapy,* Alan R. Liss, Inc., pp. 77–96).

Techniques described for the production of single chain antibodies (U.S. Pat. No. 4,946,778) can be adapted to produce single chain antibodies to immunogenic polypeptide products of this invention.

The antibodies can be used in methods relating to the localization and activity of the protein sequences of the invention, e.g., for imaging these proteins, measuring levels thereof in appropriate physiological samples and the like.

Antibodies specific to the haemopoietic maturation factor may further be used as antagonists to inhibit the proper functioning of the polypeptide. In this manner, the antibodies may be used in therapy, for example, to stimulate cell growth to treat certain disorders, for example, AIDS and anemia.

Further, such antibodies can detect the presence or absence of haemopoietic maturation factor and, therefore, are indicators of disorders of the haemopoietic and neural system. These antibodies may, therefore, be used as a diagnostic for disorders associated therewith. Prenatal diagnosis may also be particularly useful where the associated disorders are congenital.

Alternatively, an antagonist to the polypeptide of the present invention may be employed which binds to the receptors to which the polypeptide of the present invention normally binds. The antagonist is similar to an inactive form of the polypeptide and may be generated in ways similar to the ways in which antibodies specific to haemopoietic maturation factor are generated. In this way the action of the haemopoietic maturation factor is prevented and the antagonist may be used therapeutically for stimulation of cell growth to treat certain disorders, for example AIDS. The antagonist may also be used diagnostically to detect the presence or absence of haemopoietic maturation factor.

The present invention will now be further described with reference to the following examples; however, it is to be understood that the present invention is not limited to such examples. All parts or amounts, unless otherwise specified, are by weight.

In order to facilitate understanding of the following examples, certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 $\mu$g of plasmid or DNA fragment is used with about 2 units of enzyme in about 20 $\mu$l of buffer solution. For the purpose of isolating DNA fragments for plasmid construction, typically 5 to 50 $\mu$g of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., *Nucleic Acids Res.,* 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiaster bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 μg of approximately equimolar amounts of the DNA fragments to be ligated.

EXAMPLE 1

Expression and Purification of the Haemopoietic Maturation Factor

The DNA sequence encoding for haemopoietic maturation factor (ATCC #75514) is initially amplified using PCR oligonucleotide primers corresponding to the 5' and 3' end of the DNA sequence to synthesize insertion fragments. The 5' oligonucleotide primer has the sequence GACTTCATGAAAAAGACAGATATCGCAATTGCAGTGGCACTGGCTGGTTTCGCTACCGTTGCGCAAGCTGCTTCTGACTCCCTGGTGGTGTGC (SEQ ID NO:3) contains a BspHI restriction enzyme site and the ompA leader sequence followed by 21 nucleotides of haemopoietic maturation factor coding sequence (SEQ ID NO:1) starting from the codon following the methionine start codon; the 3' sequence GACTAGATCTACGAAAGAAAGACAACTTTTC SEQ ID NO:1 contains complementary sequences to BglII site, and the last 21 nucleotides of haemopoietic maturation factor coding sequence (SEQ ID NO:1). The restriction enzyme sites correspond to the restriction enzyme sites on the bacterial expression vector pQE-60 (Qiagen Inc., 9259 Eton Ave., Chatsworth, Calif. 91311). The plasmid vector encodes antibiotic resistance ($Amp^r$), a bacterial origin of replication (ori), an IPTG-regulatable promoter/operator (P/O), a ribosome binding site (RBS), a 6-histidine tag (6-His) and restriction enzyme cloning sites. The pQE-60 vector was digested with NcoI and BglII and the insertion fragments were then ligated into the pQE-60 vector maintaining the reading frame initiated at the bacterial RBS. The ligation mixture was then used to transform the E. coli strain m15/rep4 (available from Qiagen under the trademark m15/rep4). M15/rep4 contains multiple copies of the plasmid pREP4, which expresses the lacI repressor and also confers kanamycin resistance ($Kan^r$). Transformants are identified by their ability to grow on LB plates containing both Amp and Kan. Clones containing the desired constructs were grown overnight (O/N) in liquid culture in either LB media supplemented with both Amp (100 μg/ml) and Kan (25 μg/ml). The O/N culture is used to inoculate a large culture at a ratio of 1:100 to 1:250. The cells were grown to an optical density of 600 ($O.D.^{600}$) between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3–4 hours. Cells were then harvested by centrifugation. The cell pellet was solubilized in the chaotropic agent 6 Molar Guanidine HCL. After clarification, solubilized haemopoietic maturation factor was purified from this solution by chromatography on a Nickel-Chelate column under conditions that allow for tight binding by proteins containing the 6-His tag. (Hochuli, E. et al., Genetic Engineering. Principle & Methods, 12:87–98 Plenum Press, New York (1990)). Haemopoietic maturation factor (95% pure) was eluted from the column in 6 molar guanidine HCL pH 5.0 and for the purpose of renaturation adjusted to 3 molar guanidine HCL, 100 mM sodium phosphate, 10 mmolar glutathione (reduced) and 2 mmolar gluthatione (oxidized). After incubation in this solution for 12 hours the protein was dialyzed to 50 mmolar sodium phosphate.

EXAMPLE 2

Figure 4:
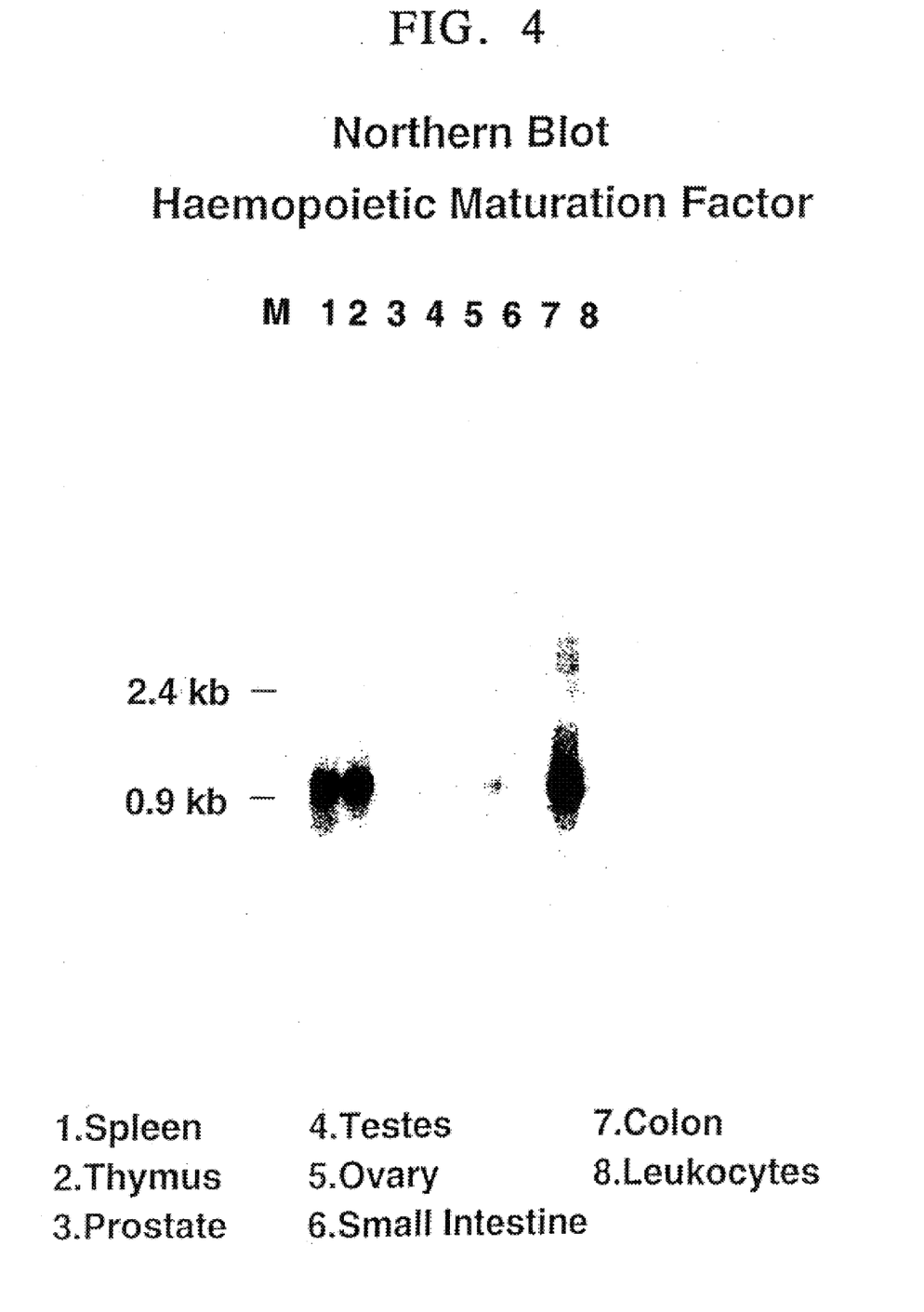
FIG. 4 is a Northern Blot analysis indicating the organs in the human body in which the haemopoietic maturation factor is predominantly found.

Expression of RNA Encoding the Haemopoietic Maturation Factor in Different Tissues In order to analyze the expression pattern of the haemopoietic maturation factor RNA was isolated from different human tissues. After total RNA isolation poly A containing RNA was isolated by affinity chromatography on a poly T containing affinity resin. Poly A containing RNA (2 ug) was separated by denaturing gel chromatography and the poly A containing RNA transferred to a membrane by blotting RNA expression pattern was determined by hybridizing the membrane bound poly A RNA to a radioactive probe spanning the haemopoietic maturation factor gene followed by auto radiography. FIG. 4.

EXAMPLE 3

Haemopoietic Maturation Factor and Inhibition of Growth of HeLa Cells

Figure 5:
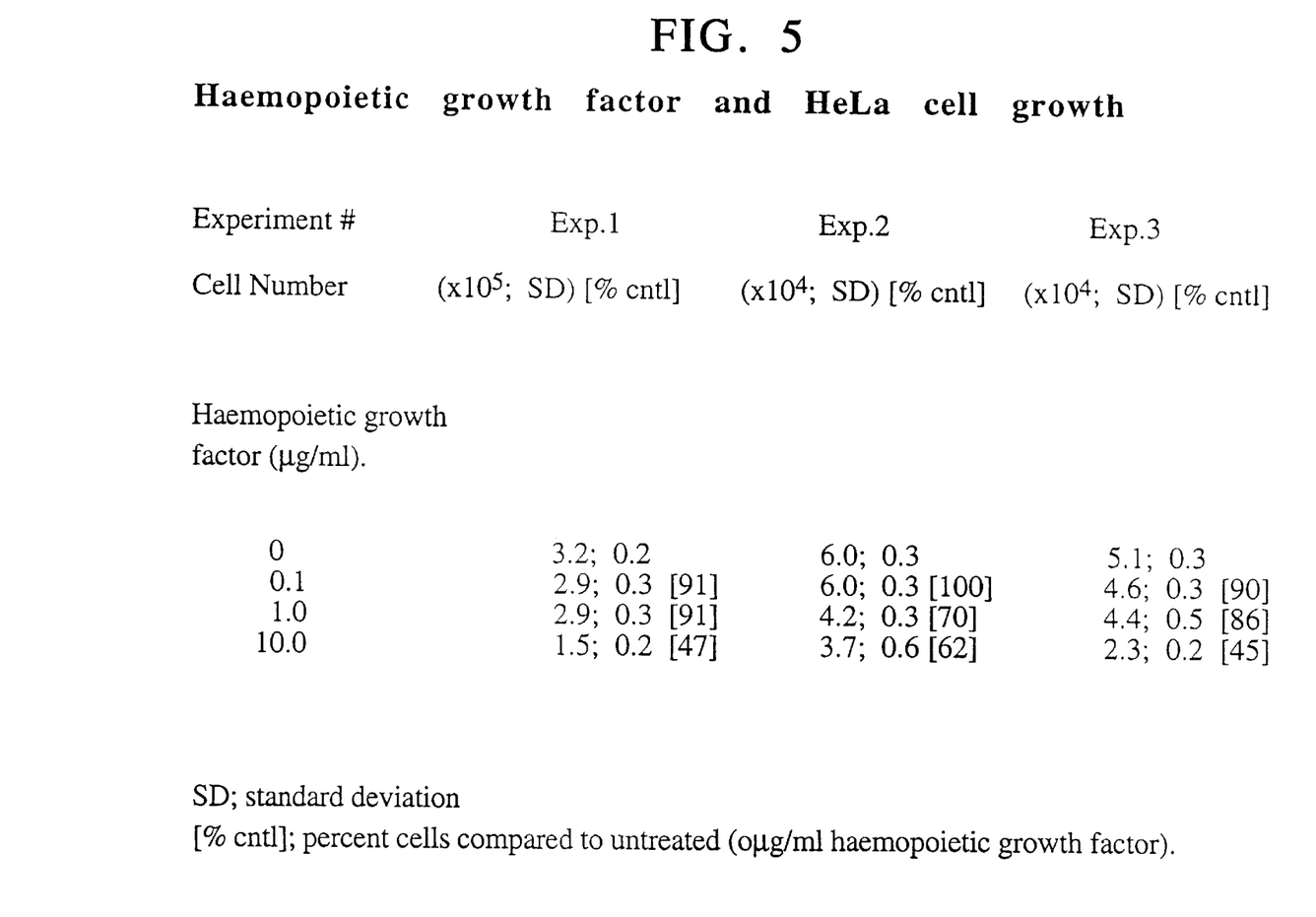
FIG. 5 illustrates that Hela cell growth is inhibited in the presence of haemopoietic maturation factor.

HeLa cells were plated at $10^5$ (experiment #1) or $10^4$ (experiment #2 and #3) per well in 24 well plates. Cells were grown in DMEM ("Dulbecco's Modified Eagle's Medium") medium (1 ml) containing 5% fetal calf serum penicillium 50 units/ml and streptomycin 50 ug/ml. Four wells were plated for each concentration of haemopoietic maturation factor per experiment. Haemopoietic maturation factor was applied one day after plating. After 3 days cells were trypsinized and counted. FIG. 5.

The results indicate that haemopoietic maturation factor inhibits the growth of cancer cells, since Hela cells are forms of cancer cells.

Numerous modifications and variations of the present invention are possible in light of the above teachings and, therefore, within the scope of the appended claims, the invention may be practiced otherwise than as particularly described.

What is claimed is:

1. An isolated polynucleotide comprising a polynucleotide sequence having at least 95% sequence identity to a member selected from the group consisting of:

(a) a polynucleotide encoding a polypeptide comprising amino acid 2 to 142 of SEQ ID NO:2; and
   (b) the complement of (a).

2. The isolated polynucleotide of claim 1 wherein said member is (a).

3. The isolated polynucleotide of claim 1 wherein said member is (a) and the polypeptide comprises amino acids 1 to 142 of SEQ ID NO:2.

4. The isolated polynucleotide of claim 1 wherein said polynucleotide sequence encodes a polypeptide comprising an amino acid sequence identical to amino acids 2 to 142 of SEQ ID NO:2.

5. The isolated polynucleotide of claim 1, wherein the isolated polynucleotide is DNA.

6. The isolated polynucleotide of claim 1 comprising a polynucleotide sequence encoding a polypeptide comprising an amino sequence identical to amino acids 1 to 142 of SEQ ID NO:2.

7. The isolated polynucleotide of claim 1, wherein said isolated polynucleotide is RNA.

8. A method of making a recombinant vector comprising inserting the isolated polynucleotide of claim 1 into a vector, wherein said isolated polynucleotide is DNA.

9. A recombinant vector comprising the isolated polynucleotide of claim 1, wherein said isolated polynucleotide is DNA.

10. A recombinant host cell comprising the isolated polynucleotide of claim 1, wherein said isolated polynucleotide is DNA.

11. A method for producing a polypeptide comprising expressing from the recombinant cell of claim 10 the polypeptide encoded by said polynucleotide sequence.

12. The isolated polynucleotide of claim 1 comprising nucleotides 49 to 471 of SEQ ID NO:1.

13. The isolated polynucleotide of claim 1 comprising nucleotides 46 to 471 of SEQ ID NO:1.

14. An isolated polynucleotide comprising a polynucleotide sequence having at least a 95% sequence identity to a member selected from the group consisting of:

(a) a polynucleotide encoding the same mature polypeptide encoded by the human cDNA in ATCC Deposit No. 75514; and (b) the complement of (a).

15. The isolated polynucleotide of claim 14, wherein the member is (a).

16. The isolated polynucleotide of claim 14, wherein said polynucleotide sequence comprises DNA identical to the coding portion of the human cDNA in ATCC Deposit No. 75514 which encodes a mature polypeptide.

17. A method of making a recombinant vector comprising inserting the isolated polynucleotide of claim 14 into a vector, wherein said isolated polynucleotide is DNA.

18. A recombinant vector comprising the isolated polynucleotide of claim 14, wherein said isolated polynucleotide is DNA.

19. A recombinant host cell comprising the isolated polynucleotide of claim 14, wherein said isolated polynucleotide is DNA.

20. A method for producing a polypeptide comprising expressing from the recombinant cell of claim 19 the polypeptide encoded by said polynucleotide sequence.

* * * * *